Sept. 3, 1968 A. THURNHER Plant Pat. 2,830
MAGNOLIA GRANDIFLORA TREE
Filed Feb. 27, 1967
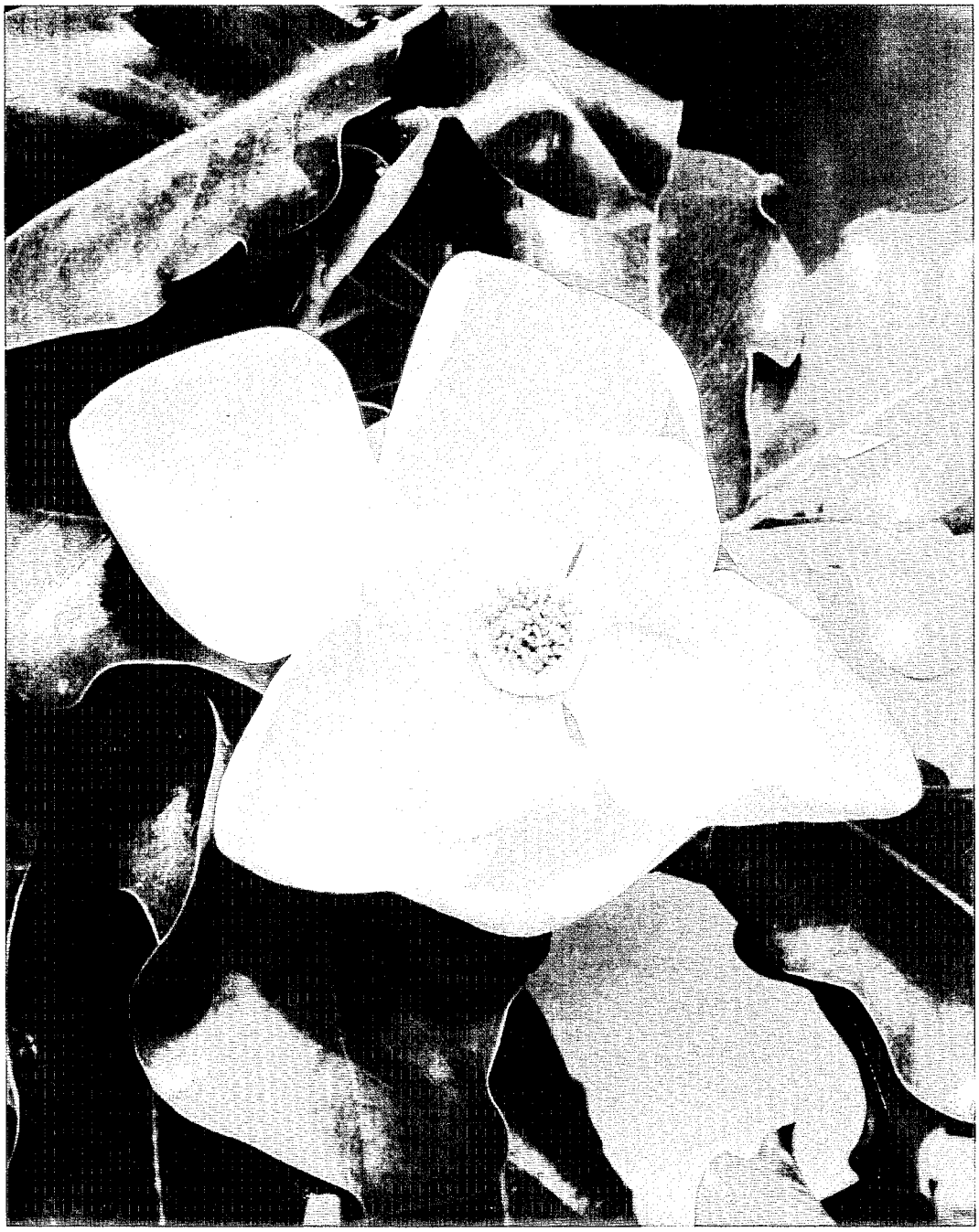
INVENTOR
Armin Thurnher
BY
Webster & Webster
ATTORNEYS

United States Patent Office

Plant Pat. 2,830
Patented Sept. 3, 1968

2,830

MAGNOLIA GRANDIFLORA TREE

Armin Thurnher, El Monte, Calif., assignor to Saratoga Horticultural Foundation, Saratoga, Calif., a non-profit corporation of California

Filed Feb. 27, 1967, Ser. No. 619,078
1 Claim. (Cl. Plt.—51)

ABSTRACT OF THE DISCLOSURE

A new and distinct variety of *Magnolia grandiflora* tree which is well adapted—because of its distinctive characteristics—for commercial reproduction, and planting as a shade and ornamental tree.

*Background of the variety.*—*Magnolia grandiflora* is indigenous to the southern part of the United States from eastern North Carolina, south to Florida, and along the Gulf of Mexico to eastern Texas. It has been widely cultivated in temperate regions of the world. United States plant patents have been issued on three varieties of this species; namely:

"Samuel Somner"—United States Plant Patent No. 2,015.
"Majestic Beauty"—United States Plant Patent No. 2,250.
"Russet"—United States Plant Patent No. 2,617.

The variety herein described is distinct—in particular comparison—from the three above-noted patented varieties in several noteworthy characteristics, as will hereinafter appear.

*Discovery of the variety.*—The herein claimed variety of *Magnolia grandiflora* tree was discovered by me in my garden at San Marino, Los Angeles County, Calif., under the following circumstances:

In a search for new and distinctive varieties of shade and ornamental trees, I gathered seeds from *Magnolia grandiflora* trees growing in and about San Marino, Calif., and from these seeds I produced a substantial number of seedlings which were maintained under careful and continuing observation. In this way, I discovered that one of such seedlings evidenced certain quite distinctive, as well as desirable, characteristics, and such one seedling (which is the instant variety) was, therefore, selected by me for asexual reproduction.

*Asexual reproduction of the variety.*—The variety was made available by me to the Saratoga Horticultural Foundation of Saratoga, Calif., and such organization—at my request—undertook asexual reproduction of the variety, and the testing and evaluation thereof. Such asexual reproduction was accomplished by cuttings and grafting, and chiefly by grafting scions of the variety on seedling-grown rootstock of *Magnolia grandiflora*. In all respects, the asexual reproductions were found to hold true to the original tree.

*Summary of the discovery.*—The present variety of *Magnolia grandiflora* is evergreen and is especially characterized by glossy, olive green leaves with strongly undulate margins; such leaves being obovate to elliptic in shape. While the leaves are glossy on the upper surface, the lower surface has a whitish, appressed tomentum scarcely visible to the naked eye. Both the individual leaves and the branches of foliage are highly decorative, outdoors and indoors, and have a long lasting quality. Further, the glossy olive green leaves with undulate margins give the tree a singular, handsome appearance quite unlike the trees of the three patented varieties hereinbefore identified.

The present variety of *Magnolia grandiflora* tree is additionally characterized by habit of growth which indicates to date that it is bushy and will be relatively small in size.

The present variety of *Magnolia grandiflora* tree is further characterized by the annular display of numerous delicate ivory white flowers having a lemon-like fragrance, and which flowers are bowl-shaped when fully open; the flower then averaging about four to seven inches in diameter. Such flowers consist of nine petals (i.e. botanically six petals and three petaloids), whereas the flowers of *Magnolia grandiflora* "Samuel Somner" (United States Plant Patent No. 2,015) and *Magnolia grandiflora* "Russet" (United States Plant Patent No. 2,617) consist of eight petals and four petaloids.

Other features of compartive difference will be indicated in the description hereinafter set forth..

*Brief description of the drawing.*—The drawing is an illustration, by photographic reproduction in color, of one of the flowers on a branchlet, together with several leaves.

*Description of the variety.*—The botanical details of the herein claimed variety of *Magnolia grandiflora* tree—with color definitions in common color terms—are as follows:

Family: Magnoliaceae.
Parentage: Unknown.
Type: Seedling.
Tree structure: This variety has a strong structural framework with well-crotched branches; the largest of the vegetatively reproduced specimens being bushy in habit of growth.
Trunk: The sturdy trunk is smooth, light grey in color, and has thin appressed scales.
Size and rate of growth: The ultimate size of the tree has not yet been determined, but observations to date indicate that the instant variety will be relatively small as compared with typical *Magnolia grandiflora* or with the trees of the three patented varieties hereinbefore identified. In Saratoga, Calif., where this new variety has been tested and evaluated, the tree grows about 18" annually in height and width; its growing period being from early May to late October.
Foliage: Evergreen.
*Texture.*—Firm and leathery.
*Shape.*—Obovate to elliptic. Apex somewhat acute or mucronate. Base cuneate, sometimes oblique. Margin entire, but strongly undulate, with a narrow, yellow-green, translucent band. Prominent midrib, slender toward the apex, with numerous small lateral veins. The most distinctive and singular characteristic of this new variety is the undulate margins of the leaves.
*Size.*—Blade varies from 4⅛" to 7¼" in length, and 2⅛" to 3" (sometimes 4") in width. Petiole varies from ⅞" to 1⅛" in length.
*Color.*—Upper surface is a glossy, olive green. Under surface has a scarcely visible whitish, appressed tomentum.
Flower buds:
*Size.*—3¼" to 3⅜" long, and 1⅛" to 1½" in diameter.
*Form.*—Narrowly ovoid, with a slender, acute apex.
*Growth.*—The bud is enclosed in a stipular spathe which splits longitudinally along a seam, and sometimes laterally along an irregular course. The spathe is usually cast by the time the flower is ready to open. The petals and petaloids are imbricated in the bud. The bud opens slowly over several days, depending on the weather.
*Peduncle.*—1¼" to 2" long, and 5/16" to ⅜" in diameter.

Flower:

*Flowering period.*—Blooms from early June to mid-August in Saratoga, Calif., with occasional blooms in September and October. Since plants of this new variety are propagated by grafting, they bloom in the first or second year. This is an advantage to the nurseryman, who will be able to assure a customer that a plant of this variety will bloom the first or second year after planting. Most seedling-grown plants of the species do not bloom for six to ten years.

*Color.*—Ivory white.

*Size.*—4" to 7" in diameter when fully opened.

*Form.*—Single and terminally borne. Bowl-shaped when fully opened. Flower has a center spindle or receptacle on which the stamens and pistils are imbricated.

*Petalage.*—6 petals borne in two alternating ranks or tiers above a tier of 3 petaloid sepals. These remain attached to the receptacle for three to five days, depending on the weather.

*Petaloids.*—The 3 petaloids are normally larger than the 6 petals, but otherwise are indistinguishable in color, form, and texture.

*Texture.*—Soft. Velvety in appearance.

*Fragrance.*—All flowers of the species *Magnolia grandiflora* noted to date have a rich, sweet fragrance. A distinct lemon-like fragrance is found in the *Magnolia grandiflora* "Russet" (United States Plant Patent No. 2,617). The present variety has somewhat the same lemon-like quality of fragrance.

*Lasting quality.*—Within the native range of *Magnolia grandiflora* there are conditions of heat, frequent rains, and high humidity during the flowering period. The flower of the species appears to be at its best in such conditions. In Saratoga, Calif., the flower of the present variety lasts for about three to five days on the tree, and about the same time as a cut flower. Those who have used this flower experimentally as a home decoration report it to be well suited to such use because of its delicately shaped petals and its daintiness in size by comparison with those of most of the other varietal forms of the species.

Floral parts:

*Stamens.*—Creamy yellow in color, imbricated in many ranks at the base of the receptacle, and early deciduous, exposing a bright purple area at the base of the receptacle.

*Anthers.*—Strap-shaped, and cream colored, with purple base. Abundant and indefinite in number.

*Filaments.*—Lower part is bright purple.

*Pollen.*—Golden yellow.

*Pistils.*—Indefinite in number, and densely imbricated on the summit of the receptacle. Style is short and recurved.

*Stigmas.*—Creamy yellow.

*Ovaries.*—Single celled and fleshy.

Fruit:

*Shape.*—Fleshy, ovate cone, 2¼" to 2¾" long, and 2⅛" to 2¼" wide at base, tapering slightly to a rounded apex, and standing upright on a peduncle 1⅛" to 1⅜" long. The fruiting body is comprised of coalescent two-seeded carpels.

*Color.*—As the fruit ripens, the green portions exposed to sunlight turn to tints of rose opal before dehiscence in October and November. At maturity, the glossy red seeds slowly emerge from the carpels.

*Seeds.*—Upon emergence from the carpels, the seeds are suspended by long, slender, while cords before falling. Two seeds are formed in each carpel. They are less than ⅜" long, and are triangular in shape.

Desirability: Hundreds of thousands of seedling-grown trees of *Magnolia gandiflora* have been propagated by commercial growers and have been planted in gardens, in parks and on streetsides and roadsides in most of the temperate parts of the world. Since most of these have been seedling-grown, they vary widely in conformation, foliage, flowers, hardiness, etc.

One of the chief advantages of carefully selecting stock of *Magnolia grandiflora* and propagating it by vegetative means is that the morphological and physiological characteristics may be predicted with a high degree of accuracy.

Thus, with the introduction of the new variety of *Magnolia grandiflora* herein described, the performance and characteristics of its vegetatively reproduced offspring can be predicted, and which include:

(1) An evergreen, rather dense appearing tree, having a strong structural framework with numerous well-crotched branches. Since it has a somewhat bushy habit of growth, indications to date are that it will be relatively small in size.

(2) Leaves which are a glossy olive green with strongly undulate margins, providing a new type of foliage of *Magnolia grandiflora* for decorative purposes, both outdoors and indoors.

(3) Numerous lemon-fragrant flowers of a delicate ivory white, giving the tree a singular note of beauty.

(4) A tree which will produce flowers in the first or second year after planting.

The tree and its flowers herein described may vary in slight detail due to climatic and soil conditions under which the variety may be grown; the present description being of the variety as grown in Saratoga, Calif.

I claim:

1. A new and distinct variety of *Magnolia grandiflora* tree, substantially as illustrated and described, characterized—as to novelty and principally in comparison with the Samuel Somner, Majestic Beauty, and Russet—by a dense-appearing, bushy-like tree having a strong structural framework with numerous well-crotched branches, singularly attractive leaves which are a glossy olive green with strongly undulate margins, and numerous lemon-fragrant ivory white flowers normally having nine petals.

No references cited.

ROBERT E. BAGWILL, *Primary Examiner.*